United States Patent [19]
Thompson et al.

[11] Patent Number: 5,616,782
[45] Date of Patent: Apr. 1, 1997

[54] METHOD OF PRODUCING ALKYL SULFOACETATE COMPOSITIONS

[75] Inventors: Ralph Thompson, Hinsdale; Ned M. Rockwell, Lake Bluff; Ann M. Michels, Libertyville; William R. Mohring, Skokie; Kevin C. Kolbe, Mt. Prospect; J. Duke Seibold, Highland Park, all of Ill.; James M. Butterwick, Old Bridge, N.J.

[73] Assignee: Stepan Company, Northfield, Ill.

[21] Appl. No.: 558,825

[22] Filed: Nov. 16, 1995

Related U.S. Application Data

[63] Continuation of Ser. No. 259,462, Jun. 14, 1994, abandoned.

[51] Int. Cl.$^6$ .......................... C07C 301/00; C07C 305/04
[52] U.S. Cl. ............................... 560/149; 424/56
[58] Field of Search ................... 424/56; 560/149

[56] References Cited

U.S. PATENT DOCUMENTS 4,807,649  2/1989  Eoga ........................................... 134/2

*Primary Examiner*—Gary Geist
*Assistant Examiner*—Dwayne C. Jones
*Attorney, Agent, or Firm*—McDonnell Boehnen Hulbert & Berghoff

[57] ABSTRACT

Disclosed are alkyl sulfoacetate compositions comprising a sulfonated ester of the formula:

$$RO(CH_2CHR_1O)_nCOCH_2SO_3M$$

where
R represents straight chain alkyl having from about 6 to 20 carbon atoms;
$R_1$ is hydrogen, methyl, or ethyl;
n is 0, or an integer of from 1 to 20; and
M represents a cation;
the composition being substantially free from monochloroacetate salts and monochloroacetic acid. These compositions are prepared by reacting an alkyl chloroester of the formula $RO(CH_2CHR_1O)_nCOCH_2Cl$ where R, $R_1$ and n are as defined above with an excess of sodium sulfite in the presence of a sulfitation catalyst at a temperature of at least about 75° C. Also disclosed are oral care compositions comprising these surfactant compositions.

15 Claims, No Drawings

METHOD OF PRODUCING ALKYL SULFOACETATE COMPOSITIONS

This is a continuation of application Ser. No. 08/259,462, filed Jun. 14, 1994 abandoned on Nov. 17, 1995.

BACKGROUND OF THE INVENTION

1. Field of the Invention

This invention relates to methods for producing salts of alkyl sulfoacetates and to alkyl sulfoacetate salt compositions. More specifically the invention relates to an improved method for preparing salts of alkyl sulfoacetates having reduced amounts of halogenated acetic acid. It also relates to sodium alkyl sulfoacetate compositions that are substantially free from monochloroacetic acid and its salts.

2. Description of the Related Arts

Sodium salts of alkyl sulfoacetates, in particular, lauryl sulfoacetate, have been recognized as being useful as surfactants in various dental care compositions. For example, sodium lauryl sulfoacetate was disclosed in U.S. Pat. No. 4,603,045 as a detergent for use in a toothpaste for cleaning natural teeth and composite tooth filling material. U.S. Pat. No. 4,807,649 discloses liquid denture cleansing compositions containing alkali metal or alkali earth metal salts of $C_{10}$–$C_{16}$ alkyl sulfoacetates. U.S. Pat. No. 3,954,962 teaches oral hygeine products that may contain sodium lauryl sulfoacetate as a detergent. In addition, alkyl sulfoacetate salts may be used in bubble baths and synthetic soap products, especially in products intended for use by individuals sensitive to soap. Sodium lauryl sulfoacetate has been used at concentrations up to about 25% in luxury-type dry foam baths.

Because alkyl sulfoacetates are added to personal care products that typically come into contact with human mucousal membranes, these surfactants must be prepared or purified to contain minimal amounts of irritating byproducts.

When alkyl sulfoacetate surfactants are manufactured, irritating starting materials are present in the surfactant mixture. These byproducts are frequently undesirable and include sodium monochloroacetate and monochloroacetic acid. These materials, and especially sodium monochloroacetate, are sensitizing agents that are substantially irritating to mucous membranes. Thus, there is a need for such surfactants having minimal amounts of these byproducts for use in personal hygiene products.

No method is currently available for the preparation or purification of an alkyl sulfoacetate substantially free of starting alkyl alcohol, monochloroacetic acid or the corresponding metal salt.

A variety of solvents have been used in attempts to purify the alkyl sulfoacetate via extraction. Each attempt results in emulsions that are virtually inseparable. Purification methods relying on precipitation of the alkyl sulfoacetate result in sulfoacetate products containing appreciable amounts of monochloroacetate impurities. Further, purification using centrifugation of the sulfoacetate yields material having substantial amounts of monochloroacetate impurities.

Without being bound by a particular theory, it is believed that purification methods based on precipitation suffer from problems caused by "micelles" that exist in solution. It is believed that the micelles entrap contaminants present in the solution as the desired material precipitates or crystallizes.

Accordingly, methods for preparing alkyl sulfoacetates that are substantially free of monochloroacetic acid and/or its salts are needed.

SUMMARY OF THE INVENTION

Methods for preparing alkyl sulfoacetate surfactants typically rely on sulfitation of a starting chlorinated alkylester with sodium sulfite. Such reactions produce sodium chloride and sodium sulfate. In addition, these methods retain undesirable materials such as monochloroacetic acid and sodium monochloroacetate. These compounds are residual or result from hydrolysis of the chlorinated alkyl ester.

Methods for preparing these surfactants may also include drying steps during which the overall yield of surfactant is reduced by hydrolysis of the product which also contributes to additional alkyl alcohol and salt byproducts such as sodium sulfoacetate. Drying of these surfactants has usually been aided by the addition of certain crisping agents such as, for example, carbonates such as sodium or potassium carbonate, bicarbonates such as sodium or potassium bicarbonate, dicalcium phosphate, hydrated alumina, silicates such as silicon dioxide, and sodium chloride or sodium sulfate.

Surfactant products intended for use in dental care and personal hygiene products must be of sufficient purity. Thus, there is a need for methods for preparing alkyl sulfoacetates having minimal, preferably non-detectable, amounts of monochloroacetic acid and sodium monochloroacetate. No method presently exists that is capable of preparing an alkyl sulfoacetate product that has non-detectable levels of monochloroacetic acid and its sodium salt.

It has been unexpectedly discovered that the overall yield and purity of alkyl sulfoacetate mixtures can be improved when the starting alkyl chloroester is sulfitated with a molar exces of sodium sulfite in the presence of a catalyst. Such conditions provide for dramatically diminished amounts of the unwanted byproducts monochloroacetic acid and sodium monochloroacetate in the final surfactant composition.

Thus, the invention provides alkyl or alkylalkoxy sulfoacetates that are substantially free from monochloroacetic acid and/or its salts.

The invention further provides surfactant compositions comprising:

(a) a sulfonated ester of formula I:

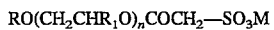

$$RO(CH_2CHR_1O)_nCOCH_2\text{—}SO_3M \qquad\qquad I$$

where

R represents straight chain alkyl having from about 6 to 22 carbon atoms;

$R_1$ is hydrogen, methyl, or ethyl;

n is 0, or an integer of from 1 to 22; and

M represents a cation, such as, for example, $Ca^{++}$, $Mg^{++}$, $Na^+$, $K^+$ or $NH_4^+$; and (b) less than about 5 ppm of solids of monochloroacetic acid and less than about 5 ppm of solids of sodium monochloroacetate.

The invention also provides methods for preparing alkyl sulfoacetates of formula I comprising reacting an alkyl chloroester of the formula $RO(CH_2CHR_1O)_nCOCH_2Cl$ where R, $R_1$ and n are defined as above with a molar excess of an aqueous sulfite in the presence of a sulfitation catalyst at a temperature of at least about 75° C. to form a sulfitation product.

The sulfitation product may subsequently be purified to remove salts and finally dried to yield a dry product.

The surfactant compositions of the invention may be used to prepare various oral care compositions. Such oral care compositions will also include foam enhancers, viscosity modifiers, carriers, polishing agents, flavoring agents, fluorides, and anti-enzyme and anti-cavity agents.

DETAILED DESCRIPTION OF THE INVENTION

As used herein, lauryl-myristyl means an about 70:30 mixture by weight of alkyl groups having 12 and 14 carbon atoms respectively.

The invention encompasses surfactant mixtures comprising a sulfonated ester of formula I that are substantially free from monochloroacetic acid and its salts, i.e., they comprise less than about 5 ppm of solids of each of monochloroacetic acid and monochloroacetate.

The surfactant mixtures prepared according to the invention are substantially free of monochloroacetic acid and sodium monochloroacetate. I.e., the levels are below the minimum detectable level. At present, 5 ppm is the lower limit of the HPLC detection system used to analyze the alkyl sulfoacetate mixtures. Thus, a presently preferred amount of monochloroacetic acid is less than about 5 ppm based on the total weight of solids in the mixture. A presently preferred amount of sodium monochloroacetate is also less than about 5 ppm of solids.

Alkyl sulfoacetates of formula I have R groups that contain from about 6 to 22 carbon atoms. These sulfoacetates may optionally be alkoxylated with up to 22 alkoxy groups. Preferred alkoxylated sulfoacetates contain from about 1 to 5 alkoxy groups. Preferred alkoxy groups are ethoxy and propoxy groups which are introduced into the molecule prior to esterification and sulfitation by treating an alkyl alcohol with ethylene, propylene or butylene oxide.

Preferred starting alkyl monochloroacetates have about 12–14 carbon atoms. Particularly preferred starting alkyl monochloroacetates are dodecyl monochloroacetate and lauryl-myristyl monochloroacetate. These monochloroacetates result in the preferred sulfoacetates sodium dodecyl sulfoacetate and sodium lauryl-myristyl sulfoacetate, respectively. Sodium lauryl-myristyl sulfoacetate is an about 70:30 mixture by weight of $C_{12}$ and $C_{14}$ sulfoacetates.

The methods for preparing compounds of formula I comprise a sulfitation reaction. The sulfitation employs an alkyl halogenated ester, preferably a chloroester, as the starting material. Alkyl halogenated esters may be prepared by reacting a $C_6$–$C_{22}$ straight or branched chain alcohol with a halogenated, preferably a chlorinated, acetic acid, optionally, in the presence of a suitable catalyst.

The sulfitation reaction comprises reacting an alkyl chloroester with an excess, usually at least about a 3% molar excess, of aqueous potassium or sodium sulfite ($K_2SO_3$ or $Na_2SO_3$). A preferred sulfite is sodium sulfite. The amount of sulfite preferably ranges from about a 15 to 50% molar excess of the sulfite. More preferred amounts are from about a 30 to 35% molar excess, while most preferred reactions employ about a 33% molar excess of the sulfite. During the sulfitation reaction, lower alcohols and glycols such as, for example, ethanol, methanol, propanol, butanol, ethylene glycol, propylene glycol, or butylene glycol may be present.

The sulfitation reaction is conducted at a temperature of at least about 75° C., preferably at least about 85° C., and most preferably from about 85°–99° C., to form a sulfitation product. Reaction temperatures sufficient to boil water may be used but, of course, require the use of a pressure vessel.

The sulfitation reaction may be conducted at any pressure that does not adversely alter the final product; i.e., the final product will be substantially free of monochloroacetic acid and/or its salts.

Reaction times of from about 10–12 hours are typical at the most preferred temperatures of about 85°–99° C. The reaction time is usually dependent on temperature. Thus, although lower temperatures may be used, longer reaction times are normally required for lower temperatures and shorter reaction times are needed at higher temperatures.

The sulfitation reaction is conducted in the presence of a sulfitation catalyst. The sulfitation catalyst may be either an iodide containing species, metallic copper, or an emulsifier. Suitable iodide containing species that may be employed as the catalyst include the iodide salts of sodium, potassium, lithium, calcium, copper (I), aluminum, manganese (II), tin (II) and (IV), and phosphorous (III).

Particularly preferred catalysts are potassium iodide and metallic copper. An effective catalytic amount of the catalyst is used during the sulfitation step; preferred amounts are from about 0.1–5% based on the total weight of reactants. More preferred amounts of the catalyst are from about 0.5 to 2% by weight. As presently practiced, the method employs potassium iodide as the catalyst at about 1% by weight of the reactants.

As indicated above, the sulfitation catalyst may be an emusifier, i.e., an emulsifier-catalyst. The emulsifier catalyst may be any emulsifier acceptable for use in oral care compositions. A preferred amount of the emulsifier-catalyst is an amount sufficient to provide an emulsion of the sulfitation reactants, e.g., at least about 0.1% by weight of the reactants.

A preferred emulsifier-catalyst is a "heel" of previously prepared alkyl sulfoacetate. The heel may contain any amount, preferably from 0.1 to 10%, and more preferably about 5%, by weight of monochloroacetic acid or its salts based on the weight of the heel. As presently practiced, alkyl sulfoacetates for use as the heel contain about 2000 ppm, i.e., 0.2% by weight of the heel, of monochloroacetic acid or its salts.

Sulfitation reaction mixtures may be prepared to contain from about 0.5 to 5% of the heel by weight of the total initial reaction mixture. A particularly preferred reaction contains about 2.5% by weight of an alkyl sulfoacetate heel.

Surprisingly, the monochloroacetic acid originally present in the reaction mixture via the heel is completely consumed by the sulfitation. Thus, the product unexpectedly is substantially free of monochloroacetates.

A buffer may be added to the sulfitation reaction to moderate the reaction pH. A preferred pH for the reaction is from about 6 to 8. Particularly preferred reactions are buffered to about pH 7. Any suitable buffer may be employed, such as, for example, hydrochloric acid, sulfuric acid or, preferably, sodium bisulfite.

The sulfitation reaction proceeds until sodium monochloroacetate and monochloroacetic acid are nondetectable. The current minimal level of detection for each of these materials, using a Dionex Chemical Supression HPLC, is 5ppm of solids. Thus, the reaction is carried out until the mixture contains less than the detectable level of each of sodium monochloroacetate and monochloroacetic acid.

The sulfitation reaction produces sodium chloride and sodium sulfate as inorganic salt products. When the levels of the sodium monochloroacetate and monochloroacetic acid are nondetectable, the inorganic salts may be removed or simply adjusted to a desirable level. A variety of methodologies exist for adjusting or removing the inorganic salts. Representative of these methods are precipitation methods, organic extraction methods, ultrafiltration and other membrane technologies, ion exchange or size exclusion chromatography and other chromatographic methods.

In certain embodiments of the invention, the method further comprises a drying step. A variety of methods may be employed for drying the sulfitation product. Among suitable drying methods are freeze drying, spray drying, drum drying, pan drying, and wiped film evaporative methods.

Subsequent to the sulfitation step, the sulfitation mixture may optionally be bleached with a bleaching agent such as hydrogen peroxide. Bleaching may be conducted at a pH of from about 5–8, and more preferably at a pH of from about 6–7.5.

The crude sulfitation product is substantially free of monochloroacetic acid and sodium monochloroacetate, i.e., the product has non-detectable levels of monochloroacetic acid and sodium monochloroacetate.

Examples of product mixtures that may be prepared by the invention are shown below:

|   | weight percent |
|---|---|
| sodium dodecyl sulfoacetate | 82–85 |
| sodium chloride | 6.0–8.0 |
| sodium sulfate | 6.0–8.0 |
| sodium sulfoacetate | 0–4 |
| dodecyl alcohol | 0–0.8 |
| sodium monochloroacetate | non-detectable |
| sodium lauryl-myristyl sulfoacetate | at least about 80 |
| sodium chloride | 6–8 |
| sodium sulfate | 6–8 |
| sodium sulfoacetate | 0–5 |
| lauryl-myristyl alcohol | 0–0.8 |
| sodium monochloroacetate | non-detectable |
| sodium lauryl-myristyl sulfoacetate | at least about 80 |
| sodium chloride | 0–15 |
| sodium sulfate | 0–15 |
| sodium sulfoacetate | 0–5 |
| lauryl-myristyl alcohol | 0–0.8 |
| sodium monochloroacetate | non-detectable |

The oral compositions of the present invention may be substantially solid or pasty in character, such as a toothpaste gel, or dental cream. The vehicle of such solid or pasty oral preparations generally contains a polishing material.

Examples of materials useful as polishing agents in the oral composition of the present invention include water-insoluble silicone polishing agents, hydrated alumina and dicalcium phosphate, including dicalcium phosphate dihydrate and anhydrous dicalcium phosphate. Siliceous polishing agents include colloidal silica xerogel, precipitated silica and sodium aluminosilicates or silica grades containing combined alumina, typically in amount of about 0.1–7% by weight. Other polishing materials include insoluble sodium metaphosphate, carbonates such as magnesium, calcium, sodium or potassium carbonate, bicarbonates such as, for example, sodium or potassium bicarbonate, calcium pyrophosphate, trimagnesium phosphate, etc. Mixtures of polishing agents may be used.

Typically, the polishing material is included in the dentifrice composition of the present invention in an amount of from about 20 to about 60% by weight and preferably from about 35 to about 55%.

The oral compositions of this invention may also contain conventional additional ingredients such as coloring or whitening agents, or preservatives such as sodium benzoate, in amounts of up to 5% by weight and preferably up to 1% provided they do not interfere with the chemical and cosmetic stability properties of the finished product.

In toothpaste, gel or dental creams, the oral composition is formulated using a water and humectant carrier typically in an amount ranging from about 10 to about 90% of the composition.

Sorbitol, typically commercially available in 70% aqueous solution, glycerine, low molecular weight polyethylene glycol (e.g., about 200 to 800) or propylene glycol exemplify humectants/carriers used to formulate the toothpaste, gel or dental compositions.

Toothpastes, creams, and gels typically contain a natural or synthetic thickener or gelling agent in proportions of about 0.1 to about 10, preferably about 0.5 to about 5 weight percent. Suitable thickeners include irish moss, gum tragacanth, starch, hydroxyethypropylcellulose, hydroxybutyl methyl cellulose, hydroxypropyl methyl cellulose, hydroxyethyl cellulose (e.g., available as Natrosol), sodium carboxymethyl cellulose poly-(methyl vinly ether/maleic anhydride) available for example as Gantrez AN 139 (GAF Corporation), and carboxyvinyl polymer for example available as Carbopol (e.g., 834, 840, 841). These Carbopol products of B.F. Goodrich Co., described in U.S. Pat. Nos. 2,798,053; 2,023,692, and 2,908,655, are essentially colloidally water-insoluble acidic carboxylic polymers of acrylic acid cross-linked with about 0.75 to about 2.0% of a cross-linking agent of polyallyl sucrose or polyallyl pentaerythritol.

The oral compositions of the present invention also include products which are substantially liquid in character, such as a mouthwash or rinse. In such a preparation the vehicle is typically a water-alcohol mixture desirably including a humectant as described below. Generally, the weight ratio of water to alcohol is in the range of from about 1:1 to about 20:1, preferably about 3:1 to 10:1 and more preferably about 4:1 to about 6:1. The total amount of water-alcohol mixture in this type of preparation is typically in the range of from about 70% to about 99.9% by weight of the preparation.

The pH of the oral compositions of the present invention is generally in the range of from about 4.5 to about 8 preferably in the range of from about 6 to about 8.0. The pH can be controlled with acid (e.g., citric acid or benzoic acid) or base (e.g., sodium hydroxide) or buffered (as with sodium citrate, benzoate, carbonate, or bicarbonate, disodium hydrogen phosphate, sodium dihydrogen phosphate, etc.)

In certain preferred forms of this invention, fluoride-providing salts having anti-caries efficacy may be incorporated in the oral compositions and are characterized by their ability to release fluoride ions in water. Among these materials are inorganic metal salts, for example, sodium fluoride, potassium fluoride, cuprous fluoride, a tin fluoride such as stannous fluoride or etanneous chlorofluoride, sodium fluorosilicate, ammonium fluorosilicate, sodium monofluorophosphate, alumina mono- and difluorophosphate.

The amount of the fluoride-providing compound is dependent to some extent upon the type of compound, its solubility, and the type of oral preparation, but it must be a nontoxic amount, generally about 0.01 to about 3.0% in the composition. In a solid oral composition such as a gel, toothpaste or cream, an amount of such fluoride providing compound which releases up to about 1% fluoride ion by weight of the preparation is considered satisfactory. Any suitable minimum amount of such compound may be used, but it is preferable to employ sufficient fluoride compound to release about 0.005% to 1%, more preferably about 0.1% of fluoride ion. Typically, in the cases of alkali metal fluorides and atannoue fluoride, this component is present in an amount up to about 25% by weight, based on the weight of the preparation, and preferably in the range of about 0.05% to 1%. In the case of sodium monofluorophosphate, the compound may be present in an amount of about 0.1–3.0%.

In a liquid oral preparation such as a mouthwash or rinse, the fluoride-providing compound is typically present in an amount sufficient to release up to about 1.0%, preferably about 0.001% to 0.5% by weight of fluoride ion. Generally, about 0.01 to about 3.0 weight percent of such compound is present.

Pyrophosphate salts having anti-tartar efficacy such as a dialkali or tetra-alkali metal pyrophosphate salts such as $Na_4P_2O_7$, $K_4P_2O_7$, $Na_4K_2P_2O_7$, $Na_2H_2P_2O_7$ and $K_2H_2P_2O_7$, long chain polyphosphates such as sodium hexametaphosphate and cyclic phosphates such as sodium trimetaphosphate are incorporated in solid oral compositions of the present invention preferably at a concentration of about 0.5 to about 8.0% by weight. In liquid oral preparations, the pyrophosphate salts are incorporated at a concentration of about 0.1 to about 3% by weight.

Antibacterial agents may also be included in the oral compositions of the present invention. Especially useful are non-cationic antibacterial agents which are based on phenolic and bisphenolic compounds, halogenated diphenyl ether, benzoate esters and carbanilides. Examples of such compounds are 4-chlorophenol, 2,2-trichloro-2-hydroxydiphenyl ether (Triclosan), esters of p-hydroxybenzoic acid, especially methyl, ethyl, propyl, butyl and benzyl esters, 3,4,4'-trichlorocarbanalide and 3,3',4-trichlorocarbanilide. Triclosan in amounts ranging from 0.03% to 1% is preferred for use in compositions of the present invention.

Nonionic antimicrobial agents such as sesquiterpene alcohols such as merolidol and barbitol are also useful in the present invention.

Tooth whitening agents may also be included in the oral compositions of the present invention. Especially useful are oxidizing agents such as calcium peroxide, sodium perborate, hydrogen peroxide, urea peroxide, peracetic acid, sodium percarbonate or any other source that, in aqueous solutions, acts as an hydrogen peroxide source. The amount of active oxygen in such oral compositions can vary from 0.7% to 5% by weight and preferably about 0.5% to about 2% by weight.

A wide variety of flavor compositions can be compounded from an extensive number of commercially available ingredients, including cinnamon oil, menthol, methyl salicylate, oil of spearmint, peppermint oil, oil of eucalyptus, oil of cloves, and various imitation flavor compositions made from synthetics alone or in combination with natural oils. The flavor additives should generally be present in amounts ranging from 2.0 to about 12% by weight of the product.

The oral composition of the present invention may be prepared by suitably mixing the ingredients in the preparation of a solid composition such as a toothpaste, a thickener such as carboxymethyl cellulose or hydroxyethyl cellulose is dispersed with a humectant, water, salts such as tetrasodium pyrophosphate, sodium fluoride, or sodium monofluorophosphate, and sweetener such as saccharin are then added and mixed. A polishing agent such as dicalcium phosphate, purified sodium lauryl sulfoacetate surfactant, foam enhancing compounds and flavor are then added. The ingredients are then mixed under vacuum for about 16–30 minutes. The resulting gel or paste is then tubed.

The oral care compositions of the invention may also include foam enhancers such as, for example, nonionic or amphoteric surfactants. Examples of suitable foam enhancers for use in oral care compositions according to the invention are described in European Patent Publication No. 0 577 238 A1.

All documents, e.g., patents and journal articles, cited above or below are hereby incorporated by reference in their entirety.

One skilled in the art will recognize that modifications may be made in the present invention without deviating from the spirit or scope of the invention. The invention is illustrated further by the following examples which are not to be construed as limiting the invention or scope of the specific procedures described herein.

EXAMPLE 1

Preparation of Lauryl-myristyl chloroacetate

Lauryl-myristyl chloroacetate (LCA) is prepared by reacting monochloroacetic acid (MCAA) with an about 70:30 mixture by weight of $C_{12}$ and $C_{14}$ straight chain fatty alcohols (lauryl-myristyl alcohol) at about a 1.1:1 molar ratio of acid to alcohol in a suitable reaction vessel equipped with heating and mixing means. The reaction is allowed to proceed at a temperature of between about 110° C.–138° C. for about 8 hours.

EXAMPLE 2

Sulfitation of Lauryl-myristyl Chloroacetate 72 lbs. of the crude lauryl-myristyl chloroacetate mixture (LCA) prepared as described above in Example 1 is added to a reaction vessel and heated to about 90° C. A sulfite solution containing 44.2 lbs. of $Na_2SO_3$, 2 lbs. of $Na_2S_2O_5$ and 0.98 lbs. of potassium iodide is prepared and transferred to the vessel.

The reactor is then heated to a temperature of 93° C. and maintained at a temperature between 90° and 97° C. for about 11 hours. HPLC analysis of the resulting slurry indicates nondetectable levels of monochloroacetic acid (MCAA), i.e., the slurry contains less than 5 ppm of MCAA and less than 5 ppm of sodium monochloroacetate and is deemed to be substantially free of the acid and its sodium salt.

COMPARATIVE EXAMPLE A

A sample of the crude lauryl-myristyl chloroacetate prepared according to the procedure set forth in Example 1 is treated according to the procedure of Example 2, except that the reaction is not conducted with any catalyst. HPLC analysis of this material reveals the presence of sodium lauryl-myristyl sulfoacetate containing greater than 100 ppm of sodium monochloroacetate.

The resulting material is then dissolved in boiling ethanol and the hot liquid is filtered to remove any solids. The filtrate is cooled and the precipitated sodium lauryl-myristyl sulfoacetate is recovered by filtration. HPLC analysis of the solid sodium lauryl-myristyl sulfoacetate indicates the presence of about 9.6 ppm of sodium monochloroacetate.

The ethanol purification is repeated and the resulting material again is analyzed by HPLC. The resulting (twice purified) sodium lauryl-myristyl sulfoacetate contains about 9 ppm of sodium monochloroacetate.

EXAMPLE 3

Sulfitation of Lauryl-myristyl Chloroacetate 72 lbs. of crude lauryl-myristyl chloroacetate prepared as described above in Example 1 is added to a reaction vessel with 1.75 lbs. of sodium lauryl-myristyl sulfoacetate containing 2000 ppm of sodium monochloroacetate. A sulfite solution containing 44.2 lbs. of $Na_2SO_3$ and 2 lbs. of $Na_2S_2O_5$ is prepared and transferred to the vessel.

The reactor is then heated to a temperature of 93° C. and maintained at a temperature of between 90° C. and 97° C. for about 11 hours. HPLC analysis of the resulting slurry indicates that the sodium lauryl-myristyl sulfoacetate is substantially free of monochloroacetic acid and its salts.

From the foregoing it will be appreciated that, although specific embodiments of the invention have been described herein for purposes of illustration, various modifications may be made without deviating from the spirit and scope of the invention.

What is claimed is:

1. A method for preparing a sulfonated ester of the formula:

$$RO(CH_2CHR_1O)_nCOCH_2SO_3M$$

where

R represents straight chain alkyl having from about 6 to 22 carbon atoms;

$R_1$ is hydrogen, methyl, or ethyl;

n is 0, or an integer of from 1 to 22; and

M represents $Ca^{++}$, $Mg^{++}$, $Na^+$, $K^+$ or $NH_4^+$;

comprising reacting an alkyl chloroester of the formula $RO(CH_2CHR_1O)_nCOCH_2Cl$ where R, $R_1$ and n are defined as above with at least about a 3% molar excess of an aqueous sulfite in the presence of from about 0.1 to 5% by weight of reactants of a sulfitation catalyst at a temperature of at least about 75° C.

2. A method for preparing a sulfonated ester according to claim 1, where the sulfitation catalyst is selected from the group consisting of iodide containing species, metallic copper and alkyl sulfoacetates.

3. A method for preparing a sulfonated ester according to claim 2, wherein the iodide containing species is selected from the group consisting of the iodides of sodium, potassium, lithium, calcium, copper, aluminum, manganese, tin, and phosphorous.

4. A method according to claim 2, wherein the molar excess is about a 15 to 50% molar excess.

5. A method according to claim 4, wherein the molar excess is about a 33% molar excess.

6. A method according to claim 5, wherein the temperature of the reaction is about 85°–99° C.

7. A method according to claim 6, wherein the amount of the catalyst is from about 0.5 to 2% based on the weight of reactants.

8. A method according to claim 1, where the sulfitation catalyst is an alkyl sulfoacetate comprising a monochloroacetate selected from the group consisting of monochloroacetic acid, alkali metal monochloroacetates, and mixtures thereof, the alkyl sulfoacetate being present in the reaction in an amount of about 0.1 to 5% based on the weight of reactants.

9. A method for preparing a sulfonated ester according to claim 1, further comprising the step of drying the sulfonated ester.

10. A method for preparing a sulfonated ester according to claim 1, further comprising the step of bleaching the sulfonated ester.

11. In a method for preparing an alkyl sulfoacetate of the formula:

$$RO(CH_2CHR_1O)_nCOCH_2SO_3M$$

where

R represents straight chain alkyl having from about 6 to 22 carbon atoms;

$R_1$ is hydrogen, methyl, or ethyl;

n is 0, or an integer of from 1 to 22; and

M represents $Ca^{++}$, $Mg^{++}$, $Na^+$, $K^+$ or $NH_4^{30}$, in which an alkyl chloroester of the formula $ROCOCH_2Cl$ where R is defined as above is reacted with sodium sulfite, the improvement comprising reacting the alkyl chloroester with at least about a 33% molar excess of aqueous sodium sulfite in the presence of at least about 0.1% by weight of reactants of a sulfitation catalyst at a temperature of from about 75°–105° C., the alkyl sulfoacetate having less than about 5 ppm of sodium monochloroacetate and less than about 5 ppm of monochloroacetic acid, the amounts of monochloroacetic acid and monochloroacetate being based on the total weight of solids.

12. A method for preparing a sulfonated ester according to claim 11, wherein the iodide containing species is selected from the group consisting of the iodides of sodium, potassium, lithium, calcium, copper, aluminum, manganese, tin, and phosphorous.

13. A method according to claim 12, where the sulfitation catalyst is an alkyl sulfoacetate comprising from about 0–10% by weight of monochloroacetate based on the weight of alkyl sulfoacetate, the alkyl sulfoacetate being present in the reaction in an amount of about 0.1 to 5% based on the weight of reactants.

14. A method according to claim 11, wherein the molar excess is about a 15 to 50% molar excess.

15. A method according to claim 11, wherein the temperature of the reaction is from about 85° to 99° C.

* * * * *